United States Patent [19]

Clark, Jr. et al.

[11] Patent Number: 5,347,018

[45] Date of Patent: Sep. 13, 1994

[54] PROCESS FOR PRODUCING SULFOLANE COMPOUNDS

[75] Inventors: Earl Clark, Jr.; Howard F. Efner; Jimmie J. Straw, all of Bartlesville, Okla.

[73] Assignee: Phillips Petroleum Company, Bartlesville, Okla.

[21] Appl. No.: 127,615

[22] Filed: Sep. 28, 1993

[51] Int. Cl.$^5$ .................. C07D 333/08; C07D 333/48
[52] U.S. Cl. ........................................ 549/84; 549/87
[58] Field of Search ...................... 549/84, 87

[56] References Cited

U.S. PATENT DOCUMENTS

| | | | |
|---|---|---|---|
| 2,578,565 | 12/1951 | Mahan et al. | 549/87 |
| 3,622,598 | 11/1971 | Willis | 549/87 |
| 4,132,683 | 1/1979 | Larsen et al. | 521/106 |
| 5,030,737 | 7/1991 | Nash | 549/87 |

FOREIGN PATENT DOCUMENTS 0263247 6/1963 Australia.

*Primary Examiner*—Glennon H. Hollrah
*Assistant Examiner*—Mary Cebulak
*Attorney, Agent, or Firm*—Lucas K. Shay

[57] ABSTRACT

A process for producing sulfolane compounds is provided which comprises: (1) contacting a conjugated diene with sulfur dioxide under conditions sufficient to synthesize a sulfolene compound whereby a mixture of the sulfolene compound and impurities comprising unreacted sulfur dioxide is produced; (2) transferring the mixture to an impurities removal vessel containing a freezing point depressant which comprises an aromatic compound; (3) removing the impurities; (4) transferring the impurities-reduced sulfolene compound to a hydrogenation reactor; (5) contacting the impurities-reduced sulfolene compound with hydrogen, in the presence of a hydrogenation catalyst, under conditions sufficient to produce a sulfolane compound; and (6) optionally recovering the sulfolane compound.

19 Claims, 2 Drawing Sheets

PROCESS FOR PRODUCING SULFOLANE COMPOUNDS

FIELD OF THE INVENTION

This invention relates to a process for producing sulfolane compounds from a conjugated diene and sulfur dioxide.

Sulfolane compounds are useful in a variety of industrial applications such as, for example, in pesticidal compositions, intermediates in the production of other organic chemicals, selective solvents to separate aromatic compounds from petroleum fractions, and selective solvents in alkylation of olefins.

Sulfolane compounds are general by prepared by catalytic hydrogenation of the corresponding sulfolene compounds. The sulfolene compounds are prepared by the reaction of a conjugated diene such as, for example, 1,3-butadiene, and sulfur dioxide at elevated temperatures.

The sulfolene compounds thus-produced are generally unstable and tend to decompose at mildly elevated temperatures into an unsaturated organic compound and sulfur dioxide. Some of these decomposed products polymerize and the resulting polymer coats the hydrogenation catalyst which is used to convert the sulfolene compounds to their corresponding sulfolane compounds. Coating with the polymer significantly reduces the activity of the hydrogenation catalyst. Moreover, unreacted sulfur dioxide and the sulfur dioxide obtained from decomposition of sulfolene compounds also interfere with the subsequent catalytic hydrogenation.

Consequently, it is necessary to reduce the temperature of the sulfolene compounds immediately after the sulfolene compounds are synthesized. However, lowering the temperature results in solidifying the sulfolene compounds. A solid sulfolene compound cannot be hydrogenated effectively to its corresponding sulfolane compound.

Therefore, processes have been developed to keep the sulfolene compounds in liquid state while lowering the temperature of the sulfolene compounds. For example, water is commonly used as a freezing point depressant to keep the sulfolene compounds from being solidified when the temperature is lowered from the reaction temperature at which the sulfolene compounds are produced. See e.g. U.S. Pat. No. 3,622,598.

One of the problems of using water as freezing point depressant is the formation of sulfur-containing, generally sulfone, polymers which inhibits the activity of the hydrogenation catalyst. Formation of a sulfur-containing polymer also decreases the yield of the desired sulfolane compounds and adds costs for separating the polymers from the sulfolene compounds.

Processes have been developed for inhibiting the formation of polymers in the production of sulfolane compounds. For example, amines have been used as inhibitors in reducing the amount of polysulfone polymer formation. See e.g. U.S. Pat. No. 3,928,385. However, there is an ever present need to develop still more effective methods of reducing the polymer formation so that the production of sulfolane compounds can be greatly improved.

Another problem of using water as freezing point depressant is the formation of nickel sulfate when Raney nickel is used to hydrogenate the sulfolene compound to the sulfolane compound. Nickel sulfate is generally regarded as environmentally undesirable. Therefore, it would be a significant contribution to the art if a process for producing sulfolane compound having reduced nickel sulfate could be developed.

SUMMARY OF THE INVENTION

An object of the invention is to reduce the formation of sulfur-containing polymer during the preparation of sulfolane compounds. Another object of the invention is to provide a process for using an aromatic compound as freezing point depressant. Still another object of the invention is to develop a process to improve the productivity of sulfolane compounds produced. An advantage of the invention is the reduction of the formation of sulfur-containing polymer and environmentally undesirable nickel sulfate. Other objects, features and advantages will become more apparent as the invention is more fully disclosed hereinbelow.

According to the present invention, a process for maintaining a sulfolene compound in liquid state is provided which comprises contacting a sulfolene compound with a freezing point depressant wherein the freezing point depressant comprises an aromatic compound, and the sulfolene compound is produced by contacting a conjugated diene with sulfur dioxide under conditions sufficient to synthesize the sulfolene compound.

DETAILED DESCRIPTION OF THE INVENTION

Figure 1:
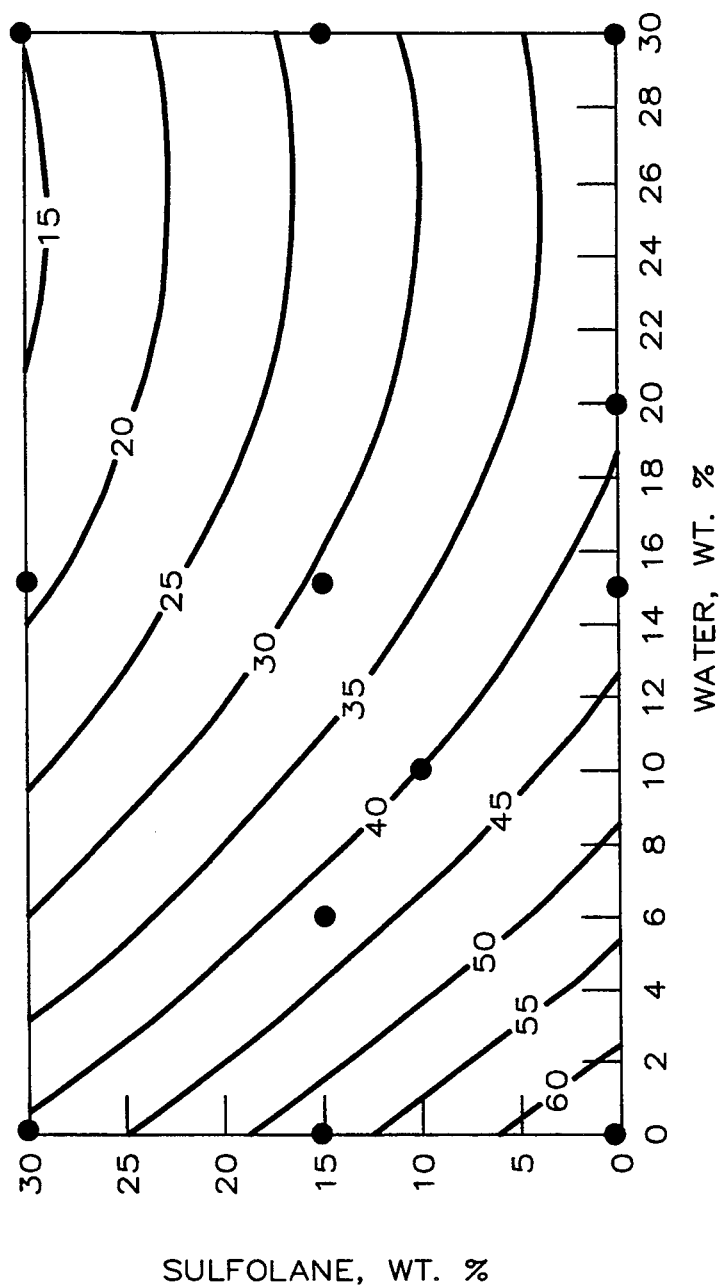
FIG. 1 is the contour plot of the fitted quadratic model which covers sulfolane and water contents of 0 to 30 weight percent, used as freezing point depressant. The detailed description as shown in Example I. The numbers in the figure are the freezing point contour lines of the sulfolene/sulfolane/water in degree C. and the circles in the figure are the data points taken in Example I.
Figure 2:
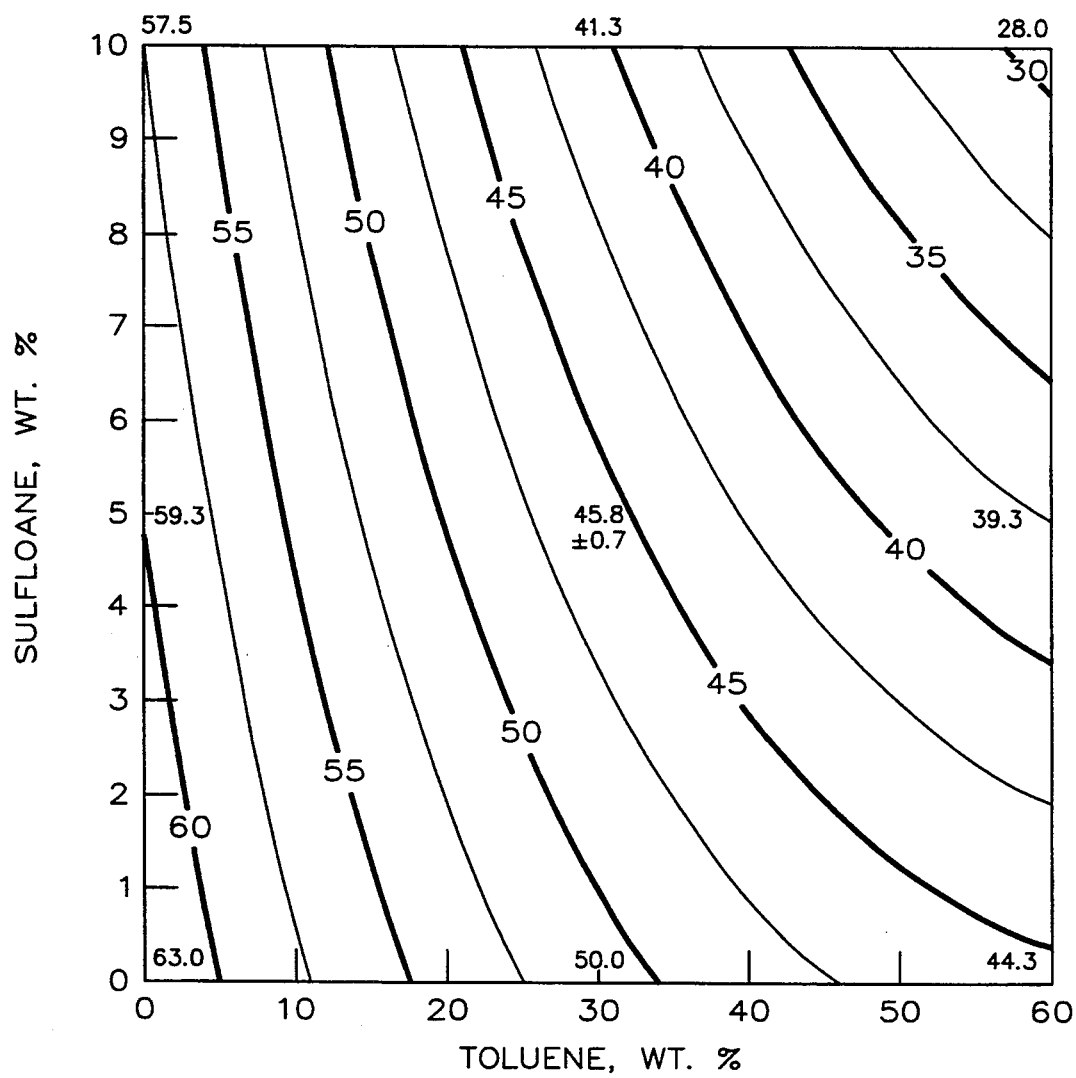
FIG. 2 is the contour plot of the fitted quadratic model which covers sulfolane and toluene contents of 0 to 10 and 0 to 60 weight percent, respectively, as detailed in Example II. The numbers in large type are the freezing point contour lines of the toluene/sulfolane/sulfolene mixture in degree C. and the numbers in small type are observed freezing points.

The term "sulfolene" (sometimes referred to as "sulfolenes" or "sulfolene compounds") as employed herein is defined in U.S. Pat. No. 3,622,598, which is incorporated herein by reference. This term includes substituted and unsubstituted 3-sulfolenes and 2-sulfolenes. The preferred sulfolene compound used in this invention is unsubstituted 3-sulfolene, which is commercially available and is produced by reaction of 1,3-butadiene and sulfur dioxide. The terms "sulfolane" and "sulfolane compounds" are also defined in U.S. Pat. No. 3,622,598.

The sulfolene compounds can be prepared by reacting sulfur dioxide with a conjugated diene having the structural formula R—C(R)=C(R)—C(R)=C(R)—R wherein each R can be the same or different and is selected from the group consisting of hydrogen and various organic and/or inorganic radicals which do not interfere with the reaction to produce the sulfolene compound or the subsequent hydrogenation reaction to produce the corresponding sulfolane compound. Inorganic radicals which are suitable include the halogens, hydroxyl groups, and mixtures thereof. Organic radicals which are preferred include hydrocarbyl substituents having 1 to 8 carbon atoms per radical.

A presently preferred class of starting materials comprises the conjugated dienes of the structural formula indicated above where each R is individually selected from the group consisting of hydrogen, alkyl, alkenyl, aryl, cycloalkyl, cycloalkenyl, aralkyl, alkaryl, alkylcycloalkyl, and combinations thereof. The total carbon content of the conjugated diene is in the range of 4 to 18.

Representative examples of the conjugated dienes include, but are not limited to, 1,3-butadiene, 2-methyl-1,3-butadiene (isoprene), 2,3-dimethyl- 1,3-butadiene, 2,3-diethyl- 1,3-butadiene, 3,4-dimethyl- 2,4-hexadiene, 2,4-dodecadiene, 2-methyl-1,3-hexadiene, 4-ethyl-1,3-hexadiene, 1-cyclopentyl-1,3-pentadiene, 1-(1-cyclohexene-1-yl)-1,3-butadiene, 2-phenyl-1,3-butadiene, 3-benzyl-1,3-pentadiene, 3-p-tolyl-1,3-pentadiene, and their homologues, and mixtures thereof. Also, suitable substituted derivatives of the above and like polyenes may be reacted with sulfur dioxide to form the desired mono-sulfones, examples of such substituted polyenes being 2-chloro-1,3-butadiene, 2-methyl-3-chloro-1,3-butadiene, 1-cyano-1,3-butadiene, and mixtures thereof.

Examples of representative sulfolene compounds include, but are not limited to, 2-methyl-3-sulfolene, 2-sulfolene, 3-sulfolene, 3-methyl-2-sulfolene, 3-methyl-3-sulfolene, 2-methyl-3-sulfolene, 2,4-dimethyl-2-sulfolene, 2,4-dimethyl-3-sulfolene, 3-ethyl-3-sulfolene, and mixtures thereof.

The term "reactor" used herein is referred to as, unless otherwise indicated, reaction vessel or vessels that can be properly employed in chemical reactions. The choice of a suitable reactor is generally a matter of preference to one ordinarily skilled in the art.

According to the present invention, a sulfolene compound is produced by contacting a conjugated diene with sulfur dioxide either in the presence or in the absence of a solvent. Preferably the synthesis is carried out in the absence of a solvent. If a solvent is used, it should be substantially miscible with the freezing point depressant of the invention. Examples of suitable solvents include alcohols, sulfones, sulfoxides, organic amides, and mixtures thereof. The weight ratio of the solvent, if present, to the conjugated diene is generally in the range of about 0.5:1 to about 1,000:1, preferably 0.5:1 to 10:1. The process of the invention can be either a continuous or a batch operation. The molar ratio of sulfur dioxide to the conjugated diene is in the range of from about 1:1 to about 2:1, preferably about 1:1 to about 1.5:1, and most preferably 1:1 to 1.2:1. The temperature of the reaction is generally in the range of from about 50° C. to about 150° C., preferably about 60° C. to about 120° C., and most preferably from 65° C. to 80° C. The pressure of the reaction vessel is generally in the range of about 10 psig to about 500 psig, preferably about 20 psig to about 300 psig, and most preferably 30 psig to 120 psig.

The order of addition of reactants to the reaction vessel is not important. Generally, the conjugated diene is added to the reaction vessel which already contains the sulfur dioxide to form a reaction mixture. The reaction mixture is allowed to react for a sufficient time, generally about 2 hours to about 24 hours, to allow substantial completion of the reaction to produce a reaction mixture comprising the sulfolene compound and impurities which contain unreacted sulfur dioxide.

Upon the desired completion of the reaction, a molten reaction effluent is transferred to an impurities removal vessel (sometimes referred to as a sulfur dioxide removal vessel) which contains a freezing point depressant. The molten sulfolene compound is generally transferred to the impurities removal vessel at the same temperature as that disclosed below for maintaining the impurities removal vessel. The freezing point depressant is generally a solvent which comprises an aromatic compound. Suitable aromatic compounds include, but are not limited to, benzene, toluene, xylenes, naphthalenes, methylnaphthalenes, biphenyl, derivatives thereof, and combinations of two or more thereof. The aromatic compounds are preferably liquid at about 20°-30° C. The derivatives can be alkyl, alkenyl, amino, halo, alkaryl, and alkaryl substituted aromatic compounds. Toluene is the presently most preferred freezing point depressant because it is readily available, it promptly decreases the freezing point of the molten sulfolene compound produced in the first step so that decomposition of the sulfolene compound is minimized, and it substantially reduces the formation of the sulfur-containing polymer. The freezing point depressant can also be or contain a sulfone compound such as, for example, sulfolane, 3-methylsulfolane, 2,4-dimethylsulfolane, 3-ethylsulfolane, and combinations of two or more thereof. The presently preferred sulfone compound is sulfolane because it is readily available.

The amount of freezing point depressant required is an amount sufficient to provide a fluid solution of the sulfolene compound and the weight ratio of the freezing point depressant to the sulfolene is generally in the range of from about 1:0.01 to about 1:100, preferably from about 1:0.05 to about 1:50, and most preferably from 1:0.1 to 1:20. The temperature of the molten reaction mixture and the freezing point depressant in the removal vessel is maintained at about 25° C. to about 100° C., preferably about 35° C. to about 80° C., and most preferably 40° C. to 70° C. to minimize the decomposition of sulfolene and the formation of undesirable polymers.

Alternatively, the freezing point depressant of the invention can also be added to the reactor which is used to synthesize the sulfolene compound. The amount and scope of the freezing point depressant and the sulfone compound employed are the same as those described above, depending on the amount of sulfolene produced.

The sulfolene compounds can optionally be recovered by any conventional means such as, for example, flaking, reprecipation from solvents, and combinations thereof. Because these means are well known to one skilled in the art, they are not detailed herein for the interest. of brevity.

After completion of the transfer, impurities including unreacted sulfur dioxide and the sulfur dioxide produced as a result of decomposition of the sulfolene compounds where the sulfur dioxide may be dissolved in the solvent employed are removed by any method known in the art such as the one disclosed in U.S. Pat. No. 3,622,598, which is incorporated herein by reference. The impurities may also be removed by sparging an inert gas to the contents in the removal vessel, under a pressure in the range of about 0.001 atmosphere (atm) to about 35 atm, preferably about 0.01 atm to about 20 atm, and most preferably 0.1 atm to 7 atm. The inert gas is generally sparged at a rate in the range of about 1 to about 100 standard cubic feet per hours (scfh), preferably about 1 to about 50 scfh, and most preferably 1 to 10 scfh. The time required for substantially removing the sulfur dioxide varies, depending oil the concentration of the sulfur dioxide and tile pressure applied, and is generally about 10 minutes to about 10 hours. The temperature for removal of the sulfur dioxide is generally in the range of about 25° C. to about 100° C., preferably about 35° C. to about 80° C., and most preferably 40° C. to 70° C. Preferably the reaction mixture is mixed during the sulfur dioxide removal with a conventional mixing means such as, for example, a mechanical mixing to facilitate the removal of sulfur dioxide.

After removing substantially most sulfur dioxide, a sulfolene compound having substantially reduced sulfur dioxide and other volatile impurities is produced. The sulfolene compound is thereafter transferred to a hydrogenation reactor followed by addition of a suitable hydrogenation catalyst. Suitable catalysts include any of those known in the art to be useful in the catalytic hydrogenation of sulfolenes to sulfolanes. A preferred class of hydrogenation catalysts are those which comprise the metal hydrogenation catalysts, such as those containing or consisting of nickel, cobalt, copper, platinum, palladium or mixtures of these metals with themselves or with other metals such as iron, zinc, chromium, cadmium, and mixtures thereof. These metals may be used in finely divided form such as, for example, Raney nickel, or may be suitably supported on a support such as kieselguhr, aluminum oxide, and diatomaceous earth. These catalysts can be prepared in any suitable manner known to one skilled in the art. The amount of catalyst utilized will vary with the catalyst but will generally be in the range of about 0.1 to about 20 weight percent based on the weight of sulfolene compounds to be hydrogenated.

The hydrogenation can be carried out by any method known in the art such as the one disclosed in U.S. Pat. No. 3,622,598, which is incorporated herein by reference. Alternatively, the hydrogenation can be carried out by adding the total hydrogenation catalyst required in about 2-10 increments to the hydrogenation reactor containing the sulfolene compounds. Every addition represents about 10% to about 50% of the total hydrogenation catalyst required. The total hydrogenation catalyst required is the amount of catalyst necessary to substantially hydrogenate all sulfolene compounds in the hydrogenation reactor. This is done by monitoring the hydrogen uptake. Hydrogen can be constantly introduced into the hydrogenation reactor and monitored by heat release or by pressurizing the reactor up and watching the pressure decrease.

The hydrogenation of the sulfolene compounds is carried out by the conditions well known to one skilled in the art. An example is disclosed in U.S. Pat. No. 3,622,598, which is incorporated herein by reference.

Following completion of the hydrogenation reaction, the sulfolane compounds can be recovered by conventional procedures. Generally, the reaction gases are vented from mixtures and then the reaction mixture is filtered to remove the spent hydrogenation catalyst followed by flash fractionation or other procedures well known to one skilled in the art.

The following examples are presented to further illustrate the invention and are not to be construed to unduly limit the scope of the invention. All reactors or vessels employed in the examples were 2 gallons in volume and equipped with an electrical heating jacket, cooling coils, a mechanical stirrer, baffles, inlets and outlets, and appropriate temperature controls.

EXAMPLE I

This comparative example shows that the freezing point of sulfolene can be decreased by water or a mixture of water and sulfolane.

The design used for the runs was a three level, two factor Box-Wilson (central composite) design with four replicates at the center point plus additional replicates at 100 percent sulfolene and 30 weight percent water/30 weight percent sulfolane. Ranges on the two factors (water and sulfolane concentration) were from 0 to 30 weight percent. A random run order was used. Additional data points were taken at 20 weight percent water/0 weight percent sulfolane, 10 weight percent water/10 weight percent sulfolane, and 6 weight percent water/15 weight percent sulfolane to confirm and further refine the model. Data were fitted to a quadradic model using commercially available software (RS/1, BBN Software, Cambridge, Mass.). The terms, which were significant at a 95% confidence interval, were retained and are shown in Equation 1.

One hundred gram samples of water/sulfolane/sulfolene mixtures shown in Table I were prepared from deionized water, distilled sulfolane, and flaked sulfolene. The mixtures were melted and allowed to cool with stirring while the temperature of the mixture was recorded vs. time. Since, as expected, the mixtures tended to supercool significantly, it was necessary to seed many of the mixtures to induce crystallization. Time/temperature plots were used to determine the freezing points and correct for supercooling. The results are shown in Table I.

TABLE I

| | Freezing Points of Water/Sulfolane/Sulfolene Mixtures | | | |
|---|---|---|---|---|
| Run No. | Water Wt. % | Sulfolane Wt. % | Sulfolene Wt. % | Observed Freezing Point °C. |
| 1 | 0 | 15 | 85 | 54 |
| 2 | 0 | 30 | 70 | 44 |
| 3 | 30 | 30 | 40 | 15 |
| 4 | 15 | 15 | 70 | 31 |
| 5 | 30 | 15 | 55 | 27 |
| 6 | 15 | 15 | 30 | 24 |
| 7 | 0 | 0 | 100 | 64 |
| 8 | 15 | 30 | 55 | 12 |
| 9 | 15 | 0 | 85 | 44 |
| 10 | 30 | 0 | 70 | 39 |
| 11 | 15 | 15 | 70 | 30 |
| 12 | 0 | 0 | 100 | 63 |
| 13 | 30 | 30 | 40 | 15 |
| 14 | 6 | 15 | 79 | 42 |
| 15 | 10 | 10 | 80 | 40 |
| 16 | 20 | 0 | 80 | 41 |
| 17 | 15 | 15 | 70 | 31 |

The results shown in Table I indicate that water, or sulfolane, or both significantly reduced the freezing point of sulfolene. FIG. 1 is the contour plot of the fitted quadratic model which covered sulfolane and water contents of 0 to 30 weight percent. On the X axis, observed freezing points for 1.5, 20, and 30 weight percent water in sulfolene were 44°, 41° and 39° C. respectively. The 95% confidence interval for the freezing point model (Equation 1) was ±5° C.

Equation 1:
$FP(°C.) = 64.973165 - 2.093728[H_2O] - 0.795788[\text{sulfolane}] + 0.04096[H_2O]^2$ where FP denotes the freezing point, [H2O is weight percent water, and [sulfolane] is weight percent sulfolane.

With either sulfolane or sulfolane/water mixtures, it was possible to operate along the 40° C. contour line. The observed freezing point for 30 weight percent sulfolane in sulfolene was 44° C. The observed freezing points of 15 weight percent sulfolane/6 weight percent water, and 10 weight percent sulfolane/10 weight percent water mixtures were 44° C., and 40° C. respectively.

EXAMPLE II

This example shows that an aromatic compound can be used as freezing point depressant for a sulfolene compound.

The design used for the runs was a three level, two factor central composite (Box-Wilson) design with five replicates at the center point plus additional replicates taken at 5 weight percent sulfolane/60 weight percent toluene, and at 10 weight percent sulfolane/60 weight percent toluene. Freezing points were obtained as described in Example I. Experimental and predicted results are found in Table II. The experimental results were fitted to a quadratic model using commercially available software (JMP, SAS Institute Inc., Cary, N.C.). The terms, which were significant at a 95% confidence interval, were retained and shown in Equation 2.

Equation 2:
$FP(°C.) = 62.220833 - 0.466339[toluene] - 0.4575[sulfolane] - 0.019917[toluene][sulfolane] + 0.0031763[toluene]^2$ where FP denotes the freezing point, [toluene] is weight percent toluene, and [sulfolane] is weight percent sulfolane.

TABLE II

Freezing Points of Toluene/Sulfolane/Sulfolene Mixtures

| Run No. | Sulfolane % | Toluene % | Sulfolene % | Obs. FP[a] | Pred. FP[b] |
|---|---|---|---|---|---|
| 101 | 5 | 30 | 65 | 45.7 | 45.8 |
| 102 | 0 | 30 | 70 | 50.0 | 51.1 |
| 103 | 0 | 60 | 40 | 44.3 | 45.7 |
| 104 | 10 | 0 | 90 | 57.5 | 57.6 |
| 105 | 10 | 60 | 30 | 27.5 | 29.1 |
| 106 | 0 | 0 | 100 | 63.0 | 62.2 |
| 107 | 5 | 30 | 65 | 45.5 | 45.8 |
| 108 | 5 | 60 | 35 | 39.0 | 37.4 |
| 109 | 5 | 30 | 65 | 45.2 | 45.8 |
| 110 | 5 | 30 | 65 | 46.5 | 45.8 |
| 111 | 10 | 30 | 60 | 41.3 | 40.5 |
| 112 | 5 | 0 | 95 | 59.3 | 59.9 |
| 113 | 5 | 30 | 65 | 46.5 | 45.8 |
| 114 | 10 | 60 | 30 | 28.5 | 29.1 |
| 115 | 5 | 60 | 35 | 39.5 | 37.4 |

[a]Obs. FP = Observed Freezing Point (°C.).
[b]Pred. FP = Predicted Freezing Point (°C.) from Equation 2.

Similar to Table I, the results in Table II demonstrate that toluene, or sulfolane, or both significantly depressed the freezing point of sulfolene. A mixture of 60 weight percent toluene and 40 weight percent sulfolene had an observed freezing point of 44° C. The addition of small quantities of sulfolane (0 to 10 weight percent) gave improvements in freezing point depression. The ranges for the fitted model (Equation 2) are 0 to 60 weight percent toluene and 0 to 10 weight percent sulfolane. Uncertainty in the data gave a 95% confidence interval of about ±1° C.

Table II also shows that good agreement was obtained between the predicted and observed freezing points.

EXAMPLE III

This is a comparative example showing a conventional process for preparing sulfolane compounds.

Several runs were carried out as follows. A 2 gallon stainless steel reactor which contained a heel of 4750 grams of sulfolene at 74° C. was charged with 4.2 g of dimethylamine. Sulfur dioxide (1412 g or 22.06 moles) and 1,3-butadiene (1135 g or 20.02 moles) were pumped in at a rate of about 4 to 6 grams per minute while maintaining operating temperature with an external electric heater. The pressure during the above feedstock addition increased to about 160 psig (1102 kPa) by the end of the butadiene addition (e.g., 3.0 hours). The reaction mixture was kept at 74° C. with stirring for 7 to 24 hours while the pressure slowly decreased to about 80 psig (551 kPa).

Part of the reaction mixture was then transferred, using a dip tube, to an impurities removal vessel containing 1000 g of water at 50° C., leaving a heel of 4750 g of sulfolene.

A 100 mm Hg vacuum was applied to the impurities removal vessel which was sparged with 3 scfh of nitrogen for 2 to 6 hours, with continuous mixing to remove most of the sulfur dioxide, while the reactor temperature was maintained at 50° C. The final sulfur dioxide concentration was 100 to 500 ppm determined by iodimetric titration with starch as indicator. Iodimetric titration was carried out by first weighing a sample (1.5 g) into an earlenmyer flask containing 75 ml deionized water. An aliquot (0.25 ml) of starch indicator solution (prepared by heating 4 g soluble starch, 40 g sodium chloride and 200 ml deionized water at boiling with stirring for 2-3 minutes followed by cooling to 25° C.) was added to the flask. The solution in the flask was then titrated with 0.01 N iodine to the starch/iodine end point. Concentration of sulfur dioxide was calculated as: ppm $SO_2$ = [ml iodine × normality iodine × 32.035 × 1,000]/sample weight (g). The final $SO_2$ concentration was in the range of from 140 ppm to 2864 ppm.

The $SO_2$-reduced sulfolene/water mixture, was transferred to a hydrogenation reactor prior to adding catalyst. Raney nickel catalyst (150 g) was weighed out on a scale, kept wet to prevent it from rapidly oxidizing and charged to the hydrogenation reactor. The reactor was pressured to 400 psig with hydrogen. Hydrogen uptake was monitored by pressure decrease. When the pressure had decreased to 200 psig, the reactor was charged back with hydrogen to 400 psig. When the pressure ceased to fall, the hydrogenation of sulfolene was considered complete. Since the hydrogenation heat of reaction is 32.1 Kcal per gram mole, the reactor medium was maintained at 50° C. by internal cooling coils with cool water, Total sulfolane produced was about 2000 g. Several runs were made by the conventional process which produced sulfone-containing polymer as high as 59.3 g per batch.

EXAMPLE IV

This example illustrates one of the invention features by transferring the reaction mixtures produced in the 2 gallon synthesis reactor described in Example III to the impurities removal vessel containing an aromatic compound.

The runs were carried out the same as those described in Example III with the exception that different freezing point depressants were added in the impurities removal vessel as noted in Table III.

TABLE III

Reduction of NiSO$_4$ and Polymer in Solfolane Preparation

| | Freezing Point Depressant in SO$_2$ Removal Vessel[a] | | | | | |
|---|---|---|---|---|---|---|
| | Toluene | Sulfolane | H$_2$O[b] | Toluene[c] | Sulfolane[d] | H$_2$O[d] |
| Initial SO$_2$ Conc'n (ppm)[e] | 18844 | 25125 | 23555 | 14806 | 21262 | 20712 |
| Final SO$_2$ Conc'n (ppm)[e] | 205 | 1313 | 1950 | 612 | 3592 | 1890 |
| Nickel used(g)[f] | 60 | 100 | 120 | 70 | 160 | 110 |
| NiSO$_4$ (g)[g] | 12.8 | 4.4 | 9.5 | 2.4 | 7.5 | 16.2 |
| Polymer (g)[g] | 0.4 | 0.8 | 21.4 | 0 | 2.3 | 31.3 |

[a] In each run, the solvent added to the impurities removal vessel was 1000 g.
[b] The quantity of butadiene and sulfur dioxide added to the 2 gallon stainless stell reactant was 3341 g and 4154 g, respectively.
[c] Toluene (225 g) was added to the 2 gallon stainless steel reactor used for synthesizing the sulfolene.
[d] Toluene (166 g) was added to the 2 gallon stainless steel reactor used for synthesizing the sulfolene.
[e] The SO$_2$ concentration measured in sulfolene in the impurities removal vessel before the SO$_2$ was removed (initial SO$_2$ concentration) and after the SO$_2$ was removed or before hydrogenation step (final SO$_2$ concentration).
[f] Raney nickel was used in hydrogenating sulfolene to sulfolane.
[g] Nickel sulfate and polymer were determined after the hydrogenation Raney nickel removal, and solvent (freezing point depressant) removal processes were completed. The nicel salts and polymer were filtered from the sulfolane using a fritted glass funnel with 25–50 micron openings. Any sulfolane remaining was extracted with acetone. The nickel salts were dissolved in water which was then evaporated to dryness. The remaining material was considered as polymer.

The results in Table III show that the sulfur dioxide concentration in the sulfolene compound was considerably lower (205 ppm and 612 ppm) for runs in which toluene was used as freezing point depressant.

Table III also shows that significant reduction in polymer formation in runs where toluene or sulfolane was used as freezing point depressant. In these runs, polymer was reduced to 2.3 g or lower per batch. For those runs using water as freezing point depressant, as much as 31.3 g of polymer was formed.

Table III further shows that the amount of nickel sulfate formed during the process for runs employing either toluene or sulfolane as freezing point depressant were generally much lower than those employing water as freezing point depressant.

In conclusion, the results shown in Table III demonstrate that an aromatic compound such as toluene and a sulfone compound such as sulfolane, when used as freezing point depressant, significantly reduced the formation of nickel sulfate and polymer during the process making sulfolane. It should be noted, as indicated in Table III, that the formation of nickel sulfate was not dependent on the amount of Raney nickel used in the hydrogenation step.

EXAMPLE V

This example illustrates that the freezing point depressant of the invention can also be added to flaked sulfolene.

The runs were carried out the same as that described in Example IV except that the 2 gallon impurities removal vessel was charged with 2000 g of flaked sulfolene and 1000 g of freezing point depressant. This mixture was heated to 50° C., applied with 100 mm Hg of vacuum, and sparged with nitrogen gas at 3 scfh to remove sulfur dioxide. The results are shown in Table IV below.

TABLE IV

Reduction of NiSO$_4$ and Polymer in Preparation of Sulfolane by Addition of Freezing Point Depressant to Flaked Sulfolene

| | Freezing Point Depressant in SO$_2$ Removal Vessel[a] | | | |
|---|---|---|---|---|
| | Toluene | Sulfolane | Water | Water |
| Initial SO$_2$ Conc'n (ppm)[b] | 604 | 582 | 431 | 629 |
| Final SO$_2$ Conc'n (ppm)[b] | 85 | 86 | 92 | 85 |
| Nickel used (g)[c] | 80 | 80 | 50 | 50 |
| NiSO$_4$ (g)[d] | 3.5 | 5.2 | 6.9 | 13.2 |
| Polymer (g)[d] | —[e] | 0.5 | 20.9 | 35.6 |

[a] In each run, the freezing point depressant added to the sulfolene in the 2 gallon impurities removal vessel was 1000 g.
[b] See footnote e in Table III.
[c] See footnote f in Table III.
[d] See footnote g in Table III.
[e] —, trace amount of polymer was detected, but it was difficult to quantify.

The results shown in Table IV, similar to those shown in Table III, demonstrate that the freezing point depressant of the present invention significantly reduced the formation of nickel sulfate and polymer during the preparation of sulfolane.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

What is claimed is:

1. A process comprising: (1) contacting a conjugated diene with sulfur dioxide under conditions sufficient to synthesize a mixture of a sulfolene compound and impurities; (2) transferring said mixture to an impurities removal vessel; (3) contacting said mixture of sulfolene compound and impurities with a freezing point depressant; (4) substantially removing said impurities to produce an impurities-reduced sulfolene compound; and (5) hydrogenating said impurities-reduced sulfolene compound under conditions sufficient to produce a sulfolane compound; wherein said impurities comprise unreacted sulfur dioxide; said freezing point depressant comprises an aromatic compound selected from the group consisting of naphthalenes, methylnaphthalenes, biphenyl, a derivative of benzene, and combinations of two or more thereof; said derivative of benzene is selected from the group consisting of alkyl, alkenyl, amino, halo, alkaryl, and alkaryl-aromatic compounds and is liquid at about 20°-30° C.; and said freezing point depressant is present in an amount sufficient to keep said sulfolene compound in liquid state.

2. A process according to claim 1 wherein said conjugated diene has the formula of R—C(R)=C(R)—C(R)=C(R)—R; wherein each R can be the same or different and is independently selected from the group consisting of hydrogen, hydroxyl radical, a hydrocarbyl radical, and mixtures -thereof; wherein said hydrocarbyl radical is selected from the group consisting of akyl, alkenyl, aryl, cycloalkyl, cycloalkenyl, aralkyl, alkaryl, alkylcycloalkyl, and combinations of two or more thereof.

3. A process according to claim 2 wherein said conjugated diene is selected from the group consisting of 1,3-butadiene, 2-methyl-1,3-butadiene, 2,3-dimethyl-1,3-butadiene, 2,3-diethyl-1,3-butadiene, 3,4-dimethyl- 2,4-hexadiene, 2,4-dodecadiene, 2-methyl-1,3-hexadiene, 4-ethyl-1,3-hexadiene, 1-cyclopentyl-1,3-pentadiene, 1-(1-cyclohexene-1-yl)-1,3-butadiene, 2-phenyl-1,3-butadiene, 3-benzyl-1,3-pentadiene, 3-p-tolyl-1,3-pentadiene and combinations of two or more thereof.

4. A process according to claim 3 wherein said conjugated diene is 1,3-butadiene.

5. A process according to claim 1 wherein said freezing point depressant is selected from the group consisting of toluene, xylenes, naphthalenes, methylnaphthalenes, biphenyl, derivatives thereof, and combinations of two or more thereof.

6. A process according to claim 5 wherein said freezing point depressant is toluene.

7. A process according to claim 1 wherein said freezing point depressant further comprises a sulfone compound selected from the group consisting of sulfolane, 3-methylsulfolane, 2,4-dimethylsulfolane, 3-ethylsulfolane, and combinations of two or more thereof.

8. A process according to claim 1 wherein the weight ratio of said freezing point depressant to said sulfolene compound is in the range of from about 1:0.001 to about 1:100.

9. A process according to claim 8 wherein said range is from about 1:0.05 to about 1:50.

10. A process according to claim 9 wherein said range is from 0.1 to 1:20.

11. A process according to claim 1 wherein said sulfolene compound is contacted with said freezing point depressant at a temperature in the range of from about 25° C. to about 100° C.

12. A process according to claim 11 wherein said range is from about 35° C. to about 80° C.

13. A process according to claim 12 wherein said range is from 45° C. to 70° C.

14. A process according to claim 1 wherein said sulfolene compound is contacted with said freezing point depressant under a pressure in the range of from about 0.001 to about 35 atmospheres.

15. A process according to claim 14 wherein said range is from about 0.01 to about 20 atmospheres.

16. A process according to claim 15 wherein said range is from 0.1 to 7 atmospheres.

17. A process for preparing a sulfolane compound comprising: (1) reacting a conjugated diene with sulfur dioxide at a temperature in the range of from about 60° C. to about 120° C. under a pressure in the range of from about 20 psig to about 300 psig for about 2 hours to about 24 hours whereby a mixture of sulfolene compound and impurities comprising unreacted sulfur dioxide is produced; wherein said conjugated diene is selected from the group consisting of 1,3-butadiene, 2-methyl- 1,3-butadiene, 2,3-dimethyl- 1,3-butadiene, 2,3-diethyl- 1,3-butadiene, 3,4-dimethyl-2,4-hexadiene, 2,4-dodecadiene, 2-methyl-1,3-hexadiene, 4-ethyl- 1,3-hexadiene, 1-cyclopentyl-1,3-pentadiene, 1-(1-cyclohexene-1-yl)-1,3-butadiene, 2-phenyl-1,3- butadiene, 3-benzyl-1,3-pentadiene, 3-p-tolyl-1,3-pentadiene, and their homologues and analogues, and mixtures thereof; (2) transferring said mixture at a temperature in the range of from about 25° C. to about 100° C. to an impurities removal vessel wherein said vessel contains a freezing point depressant selected from the group consisting of benzene, toluene, xylenes, sulfolane, 3-methylsulfolane, 2,4-dimethylsulfolane, 3-ethylsulfolane, naphthalenes, methylnaphthalenes, biphenyl, derivatives thereof, and combinations of two or more thereof; (3) removing said impurities to produce an impurities-reduced sulfolene compound; (4) transferring said impurities-reduced sulfolene compound to a hydrogenation reactor; (5) contacting said impurities-reduced sulfolene compound with hydrogen, in the presence of a hydrogenation catalyst under hydrogenation conditions sufficient to produce said sulfolane compound.

18. A process for producing sulfolane comprising: (1) contacting 1,3-butadiene with sulfur dioxide at 65° C. to 80° C. under 30 psig to 1.20 psig to produce a mixture of sulfolene and impurities comprising unreacted sulfur dioxide; (2) transferring at said mixture to an impurities removal reactor which contains toluene; (3) removing said impurities to produce an impurities-reduced sulfolene; (4) transferring said impurities-reduced sulfolene to a hydrogenation reactor; (5) contacting said impurities-reduced sulfolene compound with hydrogen, in the presence of a hydrogenation catalyst.

19. A process according to claim 7 wherein said sulfone compound is sulfolane.

* * * * *

UNITED STATES PATENT AND TRADEMARK OFFICE
CERTIFICATE OF CORRECTION

PATENT NO. : 5,347,018
DATED : September 13, 1994
INVENTOR(S) : Earl Clark, Jr. et al It is certified that error appears in the above-indentified patent and that said Letters Patent is hereby corrected as shown below:

On the title page, item [75] Inventors: add the following names,

Max H. Rock of Amarillo, Texas
    Christopher R. Tully of Borger, Texas

Signed and Sealed this

Fourteenth Day of March, 1995

Attest:

BRUCE LEHMAN

*Attesting Officer*   *Commissioner of Patents and Trademarks*